United States Patent [19]

Ishihara et al.

[11] Patent Number: 4,921,989
[45] Date of Patent: May 1, 1990

[54] Ω-SILYLALKYNYL SILANE COMPOUND AND METHOD FOR PREPARATION THEREOF

[75] Inventors: Toshinobu Ishihara; Mikio Endo; Tohru Kubota, all of Niigata; Yasuhisa Tanaka, Kanagawa, all of Japan

[73] Assignee: Shin-Etsu Chemical Co., Ltd., Tokyo, Japan

[21] Appl. No.: 359,897

[22] Filed: Jun. 1, 1989

[30] Foreign Application Priority Data

Jun. 2, 1988 [JP] Japan .................................. 63-136006

[51] Int. Cl.$^5$ ............................ C07F 7/08; C07F 7/18
[52] U.S. Cl. .................................................... 556/431
[58] Field of Search ........................................ 556/431

[56] References Cited

U.S. PATENT DOCUMENTS 2,671,099 3/1954 Frisch et al. ......................... 556/431
2,671,100 3/1954 Frisch et al. ......................... 556/431
4,800,221 1/1989 Marko .............................. 556/431 X Primary Examiner—Paul F. Shaver
Attorney, Agent, or Firm—Millen, White & Zelano

[57] ABSTRACT

The novel organosilicon compound of the invention is an ω-silylalkynyl silane compound represented by the general formula $R_3SiC \equiv C(CH_2)_nSi(CH_3)_mX_{3-m}$, in which each R is, independently from the others, a hydrogen atom, lower alkyl group or aryl group, X is a halogen atom or a lower alkoxy group, the subscript m is 0,1 or 2 and the subscript n is an integer in the range from 10 to 30 which forms a uniform monomolecular layer on a substrate surface with silyl ethynyl groups arranged in alignment. The compound can be prepared by a Grignard reaction starting form an ω-silylalkynyl halide represented by the general formula $R_3SiC \equiv C(CH_2)_nY$, in which R and n each have the same meaning as defined above and Y is a halogen atom, and a methyl alkoxy or halosilane of the formula $(CH_3)_mSiX_{4-m}$, in which X and m each have the same meaning as defined before.

10 Claims, No Drawings

ω-SILYLALKYNYL SILANE COMPOUND AND METHOD FOR PREPARATION THEREOF

BACKGROUND OF THE INVENTION

The present invention relates to novel organosilicon compounds and a method for the preparation thereof. More particularly, the invention relates to ω-silylalkynyl silane compounds suitable for forming a monomolecular layer with functionality or an accumulated layer thereof on the surface of an inorganic solid substrate and as well as to an efficient method for the preparation thereof compound by a Grignard reaction.

In the prior art, a method of forming a layer with a silane coupling agent has been proposed and conveniently practiced with an object to modify the surface property of a solid substrate. However, commercially available coupling agents have various problems, such as insufficient thickness of the layer formed therewith due to the small chain length of the organic functional groups bonded to the silicon atoms, entwinement of the side chains in the organic functional groups and intertwinement of the organic functional groups due to the change of the bond angles caused by inclusion of heteroatoms other than carbon such as nitrogen, oxygen, sulfur and the like, which cause lack of uniformity of the coating layer, for example, unevenness in the surface condition and lack of alignment of the desired functional groups on the surface of the layer.

Furthermore, incompleteness in the alignment of the functional groups on the surface can be a fatal defect in the applications in which a post-reaction between the functional groups at the terminals of the organic functional groups is required after formation of the layer as in the application of a compound having a terminal ethynyl group to a non-linear optical material or a polyacetylene as an electroconductive polymeric material.

SUMMARY OF THE INVENTION

In view of the above mentioned situation of the art, the inventors have continued extensive investigations with an object to provide an organosilicon compound capable of of forming a mono-molecular layer having excellent properties on an inorganic solid substrate leading to completion of the invention.

Thus, the invention provides ω-silylalkynyl silane compounds represented by the general formula $$R_3SiC\equiv C(CH_2)_nSi(CH_3)_mX_{3-m}, \quad (I)$$

in which each of the groups denoted by R is, independently from the others, a hydrogen atom, lower alkyl group or aryl group, X is a halogen atom or a lower alkoxy group, the subscript m is 0, 1, or 2 and the subscript n is an integer in the range from 10 to 30.

The invention also provides a novel method for the preparation of the above defined ω-silylalkynyl silane compound represented by the general formula (I) given above comprising a synthetic process by a Grignard reaction starting from a compound represented by the general formula $$R_3SiC\equiv C(CH_2)_nY, \quad (II)$$

in which R and n each have the same meaning as defined above and Y is a halogen atom, and a silane compound represented by the general formula $$(CH_3)_mSiX_{4-m}, \quad (III)$$

in which X and m each have the same meaning as defined above.

DETAILED DESCRIPTION OF THE PREFERRED EMBODIMENTS

Examples of the organosilicon compound of the invention represented by the above given general formula (I) include compounds of the following formulae:

$(CH_3)_3SiC\equiv C(CH_2)_{11}Si(CH_3)_2Cl$;
$(CH_3)_3SiC\equiv C(CH_2)_{17}SiCl_3$;
$(CH_3)_3SiC\equiv C(CH_2)_{17}Si(OCH_3)_3$;
$H(CH_3)_2SiC\equiv C(CH_2)_{17}SiCl_3$; and
$H(CH_3)_2SiC\equiv C(CH_2)_{11}Si(OCH_3)_3$, though not particularly limited thereto.

The number n in the above given general formula (I) is a determinant parameter of the thickness of the monomolecular layer formed with the silane compound of the invention. In this regard, the value of n is preferably in the range from 10 to 30 since the silane compound of which the value of n in the general formula (I) is smaller than 10 would sometimes produce a monomolecular layer having only an insufficient thickness. On the other hand, a silane compound of the general formula (I) of which the number n is larger than 30 can hardly give a monomolecular layer with good molecular alignment because of the possible entwinement of the molecular chains due to the longer than adequate chain length of the organic functional groups.

The invention also provides a method for the preparation of are above described ω-silylalkynyl silane compound of the general formula (I). The method of the invention comprises the successive steps of preparing a Grignard reagent $R_3SiC\equiv C(CH_2)_nMgY$ from the compound represented by the general formula (II) and then the Grignard reagent is reacted with the compound represented by the general formula (III).

Examples of compound represented by the general formula (II) include the compounds of the following formulae:

$(CH_3)_3SiC\equiv C(CH_2)_{11}Cl$;
$(CH_3)_3SiC\equiv C(CH_2)_{17}Cl$;
$H(CH_3)_2SiC\equiv C(CH_2)_{17}Cl$; and
$H(CH_3)_2SiC\equiv C(CH_2)_{11}Cl$.

Examples of compounds represented by the general formula (III) include silicon tetrachloride, methyl trichlorosilane, dimethyl dichlorosilane, tetramethoxy silane, dimethyl diethoxy silane, trimethoxy chlorosilane and the like.

Preparation of the Grignard reagent is performed by introducing metallic magnesium and an organic solvent as a reaction medium such as diethyl ether and tetrahydrofuran into a reaction vessel equipped with a stirrer and a reflux condenser and then adding the compound represented by the above given general formula (II) in an approximately equimolar amount to the metallic magnesium while keeping the reaction mixture at about 10° to 60° C.

The second step of the inventive method is carried out by introducing the above prepared Grignard reagent into a reaction vessel equipped with a stirrer and a reflux condenser and containing the silane compound of the above given general formula (III) dissolved in an organic solvent as a reaction medium such as diethyl ether, tetrahydrofuran, n-hexane, toluene and the like at a temperature of 0° to 40° C. In this reaction, the amount of the compound of the general formula (III) is preferably in the range from equimolar to about five times or, more preferably, from 1.2 times to twice by moles of the amount of the compound of the general formula (II). When the amount thereof is equimolar or smaller, the yield of the desired compound is decreased due to the increase in the amount of a by-product produced by the reaction of a molecule of the compound of the general formula (III) with two molecules of the compound of the general formula (II). When the amount of the compound of the general formula (III) is increased to exceed the above mentioned upper limit, on the other hand, no further increase is obtained in the selectivity of the reaction. After completion of the reaction, the precipitated magnesium salt is separated by filtration and the filtrate is freed from the solvent by distillation. The desired product compound can be purified by distillation if the compound has a boiling point in the range of temperature at which distillation of the compound can be performed with decomposition.

The inventive silane compound is used for the surface treatment of inorganic substrate materials by the method of dipping in and pulling up from or spraying of a solution of the compound prepared by diluting the compound with an organic solvent such as n-hexane, chloroform, carbon tetrachloride and the like. The coated substrate material is kept at room temperature or subjected to a heat-treatment to form a monomolecular layer of the silane compound firmly bonded to the surface of the inorganic substrate by way of, for example, the reaction of the $\equiv$SiX groups in the molecule thereof with the —OH groups on the substrate surface accompanied by the formation of covalent bonds such as siloxane linkages and the like.

The monomolecular layer obtained by the treatment with compound of this invention is stable on the substrate surface and never lost by evaporation, dissipation and the like because of the firm bonding of the layer to the surface of the inorganic substrate as mentioned above. Further, a uniform surface layer can be easily obtained due to the absence of intertwinement between the functional groups as a consequence of the unbranched structure of the organic functional groups having 10 to 30 carbon atoms bonded to the silicon atom without any heteroatoms. The thickness of the surface layer formed from the inventive compound is controllable by adequately selecting the number of the carbon atoms in the organic functional groups. Furthermore, the surface of the monomolecular layer can be modified subsequently with various kinds of functional groups by utilizing the highly reactive silyl ethynyl groups which serve as the reaction sites. For example, field-effect transistors can be processed to be modified for use as a biosensor by successively forming a monomolecular layer on the gate-electrode thereof with a compound, of this invention modifying the silyl ethynyl groups on the surface of the monomolecular layer with hydroxy groups by the addition reaction, oxidizing the hydroxy groups to aldehyde groups and reacting the aldehyde groups with amino groups of a specific protein or enzyme to form a firm bond to the gate-electrode through the monomolecular layer. Also, formation of a polyacetylene is possible by the polymerization of the silyethynyl groups on the surface of the layer owing to the uniformity of the monomolecular layer thus giving a possibility of applications for non-linear optical materials or electroconductive polymers. In addition, when the silyl ethynyl group in the inventive silane compound is, for example, a dimethylsilyl ethynyl group, lamination of monomolecular layers through strong siloxane bonds can be carried out by the conversion of the siliconbonded hydrogen atoms in the monomolecular layer to silanolic hydroxy groups followed by the reaction thereof with a silane compound of this invention. By repeating this process, several monomolecular layers can be accumulated with strong bonding by the siloxane linkages between the layers.

Examples of the invention are given in the following.

Example 1.

19-Trimethylsilyl-18-nonadecynyl chloride of the formula $(CH_3)_3SiC\equiv C(CH_2)_{17}Cl$ in an amount of 0.5 mole was added dropwise at 50° to 60° C. over a period of 2 hours to 0.5 mole of metallic magnesium and 300 ml of tetrahydrofuran contained in a 500 ml glass flask equipped with a stirrer, reflux condenser, thermometer and dropping funnel followed by aging of the reaction mixture at 65° C. for 2 hours after completion of the dropwise addition of the reactant to give a Grignard mixture.

The Grignard mixture thus prepared was added dropwise over a period of 2 hours at 20° C. or below to an ice-chilled mixture of 1.0 mole of tetrachlorosilane and 300 ml of n-hexane contained in a glass flask of 1 liter capacity equipped with a stirrer, reflux condenser, thermometer and dropping funnel followed by aging of the reaction mixture at 30° C. for 1 hour after completion of the dropwise addition of the Grignard mixture.

Then the reaction mixture was filtered with suction to remove the precipitates of magnesium chloride and the filtrate was freed from tetrahydrofuran, n-hexane and unreacted tetrachlorosilane by stripping. Distillation of the thus obtained liquid product gave a compound boiling at 212° C. under a pressure of 1 mmHg, which could be identified by analysis to be the desired compound 19-trimethylsilyl-18-nonadecynyl trichlorosilane of the formula $(CH_3)_3SiC\equiv C(CH_2)_{17}SiCl_3$. The yield of the product was about 70% of the theoretical value.

Following are the results of the analysis undertaken for the identification of the compound by the mass spectrmetry, nuclear magnetic resonance spectrometry and infrared absorption spectrometry.

Peaks in the mass spectrum: m/z (relative intensity): *468(0.7); *453(3); *395(1); *325(7); 169(9); 154(19); 73(100); 59(19); 55(10); 43(9); 41(7). Note: The peaks marked with asterisk (*) were each accompanied by a peak of the ions with the chlorine isotope $^{37}Cl$.

Nuclear magnetic resonance: δ(ppm):

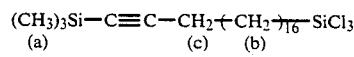

(a): 0.12 ppm(S); (b): 1.25 ppm(M); (c): 2.15 ppm(T).

Infrared absorption spectrum: cm$^{-1}$: 2930,2860: —CH$_2$—, 2195: —C$\equiv$C—, 1475: —CH$_2$—, 1258,840,760,690: Si—CH$_3$.

Example 2.

Preparation of a Grignard mixture was conducted in substantially the same manner as in Example 1 excepting the replacement of 19-trimethylsilyl-18nonadecynyl chloride with the same molar amount of 13-trimethylsilyl-12-tridecynyl chloride of the formula $(CH_3)_3SiC\equiv C-(CH_2)_{11}Cl$ and the dropwise addition thereof was carried out at 50° to 60° C.

The Grignard mixture thus prepared was added dropwise taking over 2 hours at 20° C. or below to an ice-chilled mixture of 1.0 mole of dimethyl dichlorosilane and 300 ml of toluene contained in a 1 liter glass flask equipped with a stirrer, reflux condenser, thermometer and dropping funnel followed by aging of the reaction mixture at 30° C. for 1 hour after completion of the dropwise addition of the Grignard mixture. The reaction mixture was filtered with suction to remove the precipitates of magnesium chloride and the filtrate was freed from tetrahydrofuran, toluene and unreacted dimethyl dichlorosilane by distillation. Distillation of the thus obtained liquid product gave a compound boiling at 149° C. under a pressure of 1 mmHg, which could be identified by analysis to be the desired compound 13-trimethylsilyl-12-tridecynyl dimethyl chlorosilane of the formula $(CH_3)_3SiC{\equiv}C(CH_2)_{11}Si(CH_3)_2Cl$. The yield of the product was about 82% of the theoretical value.

Following are the results of the analysis undertaken for the identification of the compound by the mass spectrmetry, nuclear magnetic resonance spectrometry and infrared absorption spectrometry:

Peaks in the mass spectrum: m/z (relative intensity): *329(41); 236(2); 221(6); 207(2); 193(4); 179(4); 168(7); 154(17); 139(17); 125(17); 111(17); *93(46); 73(100); 59(59); 45(6); 43(7); 41(9). Note: The peaks marked with an asterisk (*) were each accompanied by a peak of the ions with the chlorine isotope $^{37}Cl$.

Nuclear magnetic resonance: δ(ppm):

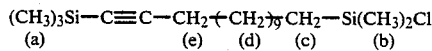

(a): 0.1 ppm(S); (b): 0.38 ppm(S); (c): 0.75 ppm(T); (d): 1.29 ppm(M); (e): 2.13 ppm(T).

Infrared absorption spectrum: cm$^{-1}$: 2970: —CH$_3$ 2920,2845: —CH$_2$— 2180: —C≡C— 1460: —CH$_2$— 1255,840,760: Si—CH$_3$.

Example 3.

Preparation of a Grignard mixture was conducted in substantially the same manner as in Example 2 excepting the replacement of 13-trimethylsilyl-12-tridecynyl chloride with the same molar amount of 13-dimethylsilyl-12-tridecynyl chloride of the formula $(CH_3)_2HSiC{\equiv}C-(CH_2)_{11}Cl$. The Grignard mixture thus obtained was added dropwise taking 2 hours at 30° C. or below to an ice-chilled mixture of 1.5 moles of tetramethoxy silane and 300 ml of n-hexane contained in a 1 liter glass flask equipped with a stirrer, reflux condenser, thermometer and dropping funnel followed by aging at 30° C. for 1 hour after completion of the dropwise addition of the Grignard mixture. The reaction mixture was filtered with suction to remove the precipitated magnesium salt. The filtrate was freed from tetrahydrofuran, n-hexane and unreacted tetramethoxy silane by stripping. Distillation of the thus obtained product gave a compound boiling at 152° C. under a pressure of 1 mmHg, which could be identified by analysis to be the desired compound 13-dimethylsilyl-12-tridecynyl trimethoxy silane of the formula $H(CH_3)_2SiC{\equiv}C(CH_2)_{11}Si(OCH_3)_3$. The yield of the product was about 65% of the theoretical value.

Following are the results of the analysis undertaken for the identification of the compound by the mass spectrmetry, nuclear magnetic resonance spectrometry and infrared absorption spectrometry:

Peaks in the mass spectrum: m/z (relative intensity): 358(2); 343(6); 311(2); 289(2); 261(2); 237(4); 231(4); 219(6); 205(6); 179(6); 165(17); 135(6); 121(100); 91(32); 59(24); 45(4); 43(6); 41(7); 39(2).

Nuclear magnetic resonance: δ(ppm):

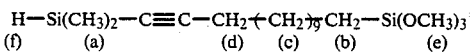

(a): 0.17 ppm(D); (b): 0.55 ppm(T); (c): 1,25 ppm(M); (d): 2.15 ppm(T); (e): 3.43 ppm(S); (f): 4.02 ppm(Q).

Infrared absorption spectrum: cm$^{-1}$: 2920: —CH$_2$, 2845: —OCH$_3$, 2180: —C≡C—, 2140: SiH, 1460: —CH$_2$—, 1255:: Si—CH$_3$, 1090: SiOC, 880: SiH, 835,815: SiCH$_3$.

What is claimed is:

1. An ω-silylalkynyl silane compound represented by the general formula

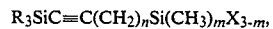

in which each of the groups denoted by R is, independently from the others, a hydrogen atom, lower alkyl group or aryl group, X is a halogen atom or a lower alkoxy group, the subscript m is 0, 1 or 2 and the subscript n is an integer in the range from 10 to 30.

2. The ω-silylalkynyl silane compound as claimed in claim 1 in which said lower alkyl group is a methyl group or an ethyl group.

3. The ω-silylalkynyl silane compound as claimed in claim 1 in which said aryl group is a phenyl group or a tolyl group.

4. The ω-silylalkynyl silane compound as claimed in claim 1 in which said halogen atom is a chlorine atom or a bromine atom.

5. The ω-silylalkynyl silane compound as claimed in claim 1 in which said lower alkoxy group is a methoxy group or an ethoxy group.

6. 19-Trimethylsilyl-18-nonadecynyl trichlorosilane of the formula $(CH_3)_3SiC{\equiv}C(CH_2)_{17}SiCl_3$, a compound of claim 1.

7. 13-Trimethylsilyl-12-tridecynyl dimethyl chlorosilane of the formula $(CH_3)_3SiC{\equiv}C(CH_2)_{11}Si(CH_3)_2Cl$, a compound of claim 1.

8. 13-Dimethylsilyl-12-tridecynyl trimethoxy silane of the formula $H(CH_3)_2SiC{\equiv}C(CH_2)_{11}Si(OCH_3)_3$, compound of claim 1.

9. The ω-silylalkynyl silane compound as claimed in claim 1 in which said lower alkyl group is methyl or ethyl, said aryl group is phenyl or tolyl, said halogen atom is chlorine or bromine, and said lower alkoxy group is methoxy or ethoxy.

10. The ω-silylalkynyl silane compound as claimed in claim 1 in which two of the R groups are methyl and the other is hydrogen or methyl and X is a chlorine or bromine atom.

* * * * *